United States Patent [19]

Cosentino

[11] 4,405,319
[45] Sep. 20, 1983

[54] POROUS TITANIUM COATING FOR BLOOD ACCESS DEVICE

[75] Inventor: Louis C. Cosentino, Wayzata, Minn.

[73] Assignee: Renal Systems, Inc., Minneapolis, Minn.

[21] Appl. No.: 303,348

[22] Filed: Sep. 18, 1981

Related U.S. Application Data

[63] Continuation-in-part of Ser. No. 261,719, May 8, 1981, which is a continuation of Ser. No. 138,579, Apr. 8, 1980.

[51] Int. Cl.$^3$ .............................................. A61M 5/00
[52] U.S. Cl. ..................................................... 604/175
[58] Field of Search ................... 3/1, 1.9; 433/9, 173, 433/201; 128/214 R, 247, 1 R; 604/28, 29, 174, 175, 280, 284, 8; 428/311

[56] References Cited

U.S. PATENT DOCUMENTS

| | | | |
|---|---|---|---|
| 3,402,710 | 9/1968 | Paleschuck | 128/1 |
| 3,452,366 | 7/1969 | Downey | 3/1 |
| 3,547,119 | 12/1970 | Hall et al. | 604/29 X |
| 3,643,658 | 2/1972 | Steinemenan | 3/1 UX |
| 3,663,965 | 5/1972 | Lee et al. | 128/214 R |
| 3,765,032 | 10/1973 | Palma | 128/1 R |
| 3,783,868 | 1/1974 | Bokros | 128/214 R |
| 4,015,601 | 4/1977 | Bokros et al. | 128/1 R |
| 4,073,999 | 2/1978 | Bryan et al. | 428/311 |
| 4,092,983 | 6/1978 | Slivenko | 128/214 R |
| 4,101,984 | 7/1978 | MacGregor | 3/1 |
| 4,108,173 | 8/1978 | Slivenko et al. | 128/1 R |
| 4,108,174 | 8/1978 | Slivenko | 128/214 R |
| 4,142,528 | 3/1979 | Whelan, Jr. et al. | 604/284 |
| 4,164,221 | 8/1979 | Bentley et al. | 128/214 R |
| 4,344,435 | 8/1982 | Aubin | 3/1 X |
| 4,375,816 | 3/1983 | Labianca | 604/8 |

FOREIGN PATENT DOCUMENTS

| | | | |
|---|---|---|---|
| 2049513 | 3/1971 | France | 3/1 |
| WO80/02107 | 10/1980 | PCT Int'l Appl. | 3/1 |
| 2000684 | 1/1979 | United Kingdom . | |
| 2019219 | 10/1979 | United Kingdom | 128/247 |
| 2056282 | 3/1981 | United Kingdom . | |

OTHER PUBLICATIONS

Proceedings of Seventh Annual Contractors' Conference of the Artificial Kidney Program of the National Institute of Arthritis, Metabolism and Digestive Diseases, pp. 160–161, (1974).
H. Tenckhoff, Chronic Peritoneal Dialysis Manual, FIGS. I-VII.
Brochure, "Pyrolite (R) Carbon Coating for Prosthetic Devices," General Atomic Corp. (1974).
"Reciprocating Peritoneal Dialysis with a Subcutaneous Peritoneal Catheter," Dialysis and Transplantation, vol. 7, pp. 834–835 and 838, (Aug. 1978).
Mpls, Medical Research Foundation, Mpls., MN, "Implantable Subcutaneous Blood Access with a Percutaneous, Puncturable Septum," excerpt from the 11th Annual Contractors' Conference, Jan. 16-18, 1978.
Mpls. Medical Research Foundation, Mpls., MN, "Evaluation of Implantable Subcutaneous Carbon Blood Access Device with Percutaneous Spigot Valve," excerpt from the 11th Annual Contractors' Conference of Artificial Kidney Program, etc., Jan. 16-18, 1978.
Brochure, "Bentley BioCarbon (R) Vascular Access System," Bentley Laboratories, Inc. (1981).

*Primary Examiner*—Richard J. Apley
*Assistant Examiner*—Michelle N. Lester
*Attorney, Agent, or Firm*—Schroeder, Siegfried, Vidas & Arrett

[57] ABSTRACT

An implantable blood access device has a matte titanium finish on the exterior subcutaneous surfaces thereof providing sites for tissue ingrowth. A preferred finish is a coating of porous titanium which may be manufactured by fusing titanium powder to the device.

8 Claims, 3 Drawing Figures

POROUS TITANIUM COATING FOR BLOOD ACCESS DEVICE

DESCRIPTION

This application is a continuation in part of copending application Ser. No. 261,719, filed May 8, 1981, which is a continuation of application Ser. No. 138,579, filed Apr. 8, 1980, for a blood access device. The entire specification of application Ser. No. 261,719 is incorporated herein by reference.

BACKGROUND OF THE INVENTION

The present invention is directed to an implantable device providing access to blood circulatory system. In particular, the invention relates to a coating on the subcutaneous surfaces of the device which facilitates tissue ingrowth.

The device in copending application Ser. No. 261,719 is an implantable generally tubular T-shaped structure in which the stem of the T is constructed and arranged to cooperate with a novel needle structure that penetrates septum seal means at the junction of the stem of the T with the balance of the T structure. By reason of the structure of the invention, the interior stem portion of the T can be rinsed clean and sterilized between each use without elaborate procedures, thus minimizing the likelihood of infection as a result of access to the circulatory system.

BRIEF DESCRIPTION OF THE INVENTION

As disclosed in application Ser. No. 261,719, a collar member of porous plastic material such as polyethylene terephthalate on the subcutaneous exterior surfaces of the implantable T-shaped device may be used to promote tissue growth onto the device. Tissue ingrowth anchors the device onto the skin. If the external surface of the device is titanium, the titanium may have a matte surfaces as an alternative to the porous plastic collar.

The present invention relates to matte surface type titanium devices. In particular, the invention is directed to devices having a subcutaneous exterior coating of porous titanium or titanium mesh. As is more fully described hereinafter, devices having a matte or porous titanium surface have advantages over those containing a porous plastic collar in that they are less bulky and there is no need for a body compatible adhesive to hold the collar to the device. Furthermore, the coating may conveniently be extended along the arms of the T to facilitate direct implantation of the device without the need for intermediate polymeric vessel grafts.

DETAILED DESCRIPTION OF THE INVENTION

Figure 1:
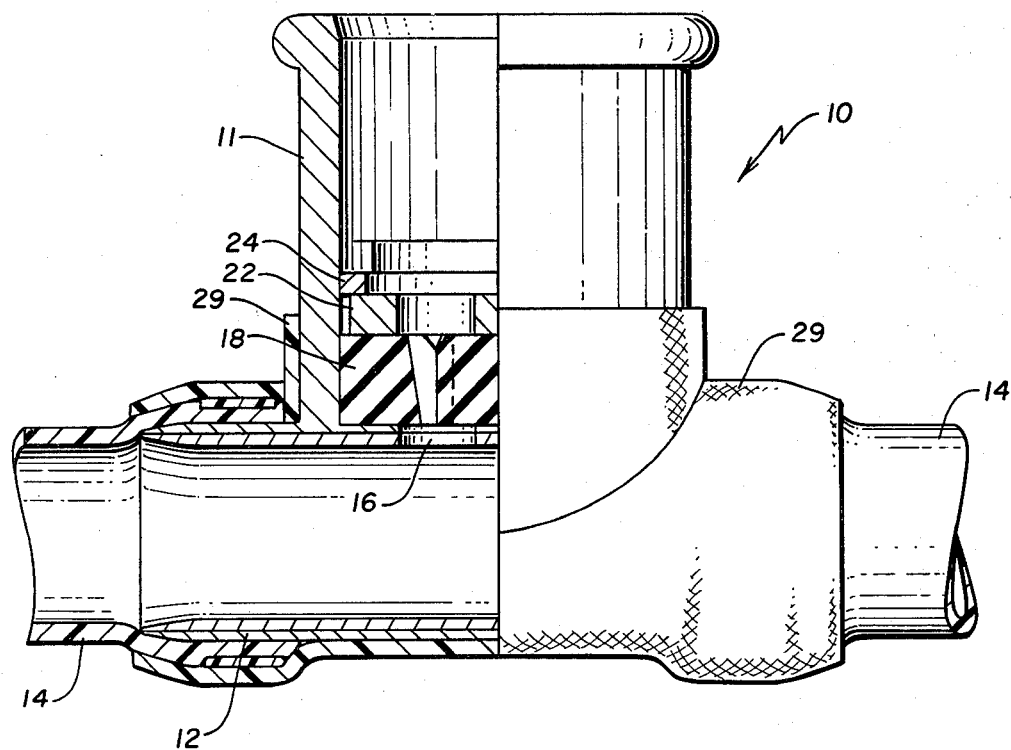
FIG. 1 is a side elevational view, partly in section, of a device in accordance with copending application Ser. No. 261,719, including a polyethylene terephthalate collar member.

Referring to the drawings, there will be seen in FIG. 1 a blood access device similar to that shown in application Ser. No. 261,719 which includes a T-shaped unitary tubular body generally designated 10 having a stem portion 11 and a straight tube portion 12 Body 10 is formed of a unitary body of biologically compatible material such as titanium. Expanded tetrafluoroethylene tubes 14 are shown joined to the ends of straight tube portion 12 by slipping over these ends. Tubes 14 provide an intermediate polymeric vessel graft between the patient's natural vessels and the tubular blood access device.

At least one internal opening 16 provides fluid communication between the stem of the T and the arms thereof. Opening 16 is sealed by septum means 18 in the cavity of stem 11. Removable septum retaining means above the septum permit periodic removal and replacement of the septum. In the embodiment shown in FIG. 1, the septum retaining means comprises a pressure plate 22 and a retaining ring 24 which is fitted into a groove in the T stem.

Covering the surfaces of device 10 below the skin is a collar member 29 of a porous plastic material such as polyethylene terephthalate, sold by E. I. DuPont, under the Trademark DACRON. The portion of stem 11 above the dermis region is uncoated to reduce the risk of infection occurring by bacteria making their way along the collar 29. Collar member 29 facilitates anchoring of the device securely under the skin by providing a site for tissue ingrowth. As shown in FIG. 1, when polymeric intermediate grafts 14 are used the collar member may surround the joint between grafts 14 and the ends of tube portion 12.

Figure 3:
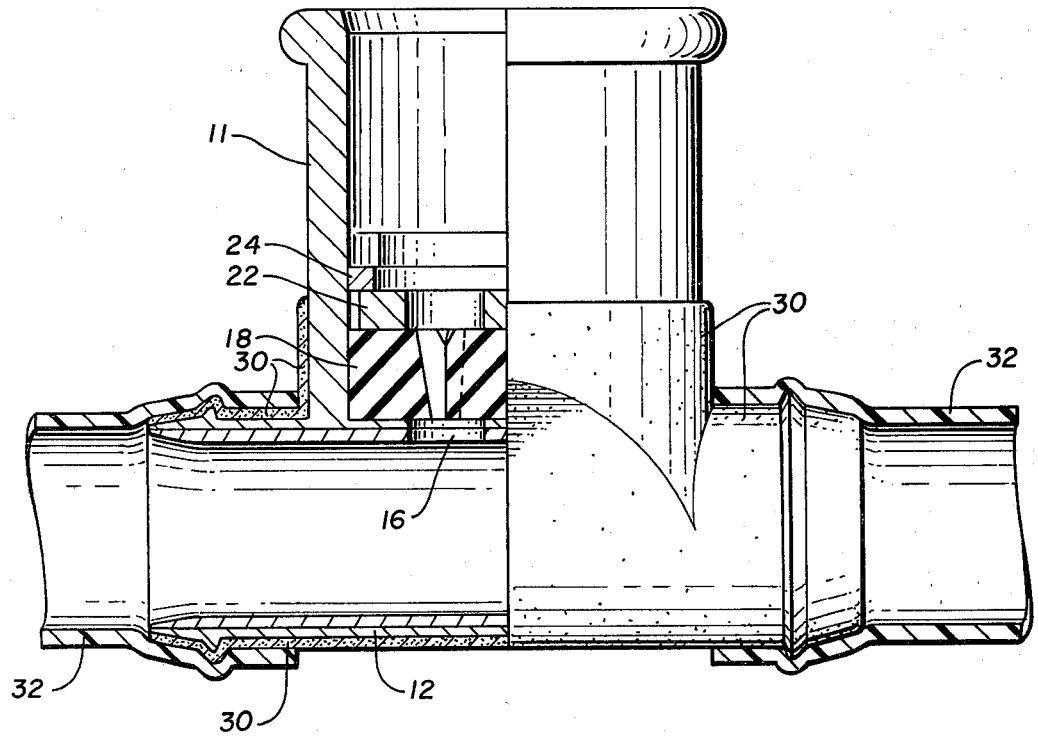
FIG. 3 is an implantable blood access device as in FIG. 2 but adapted for direct connection to natural vessels.
Figure 2:
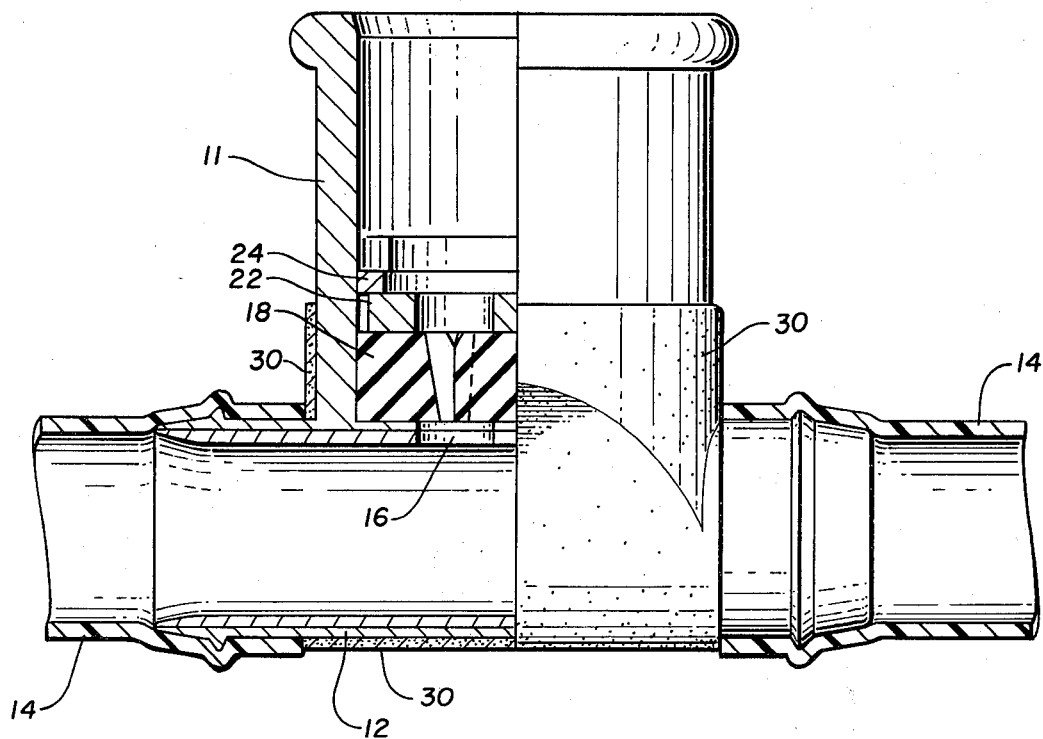
FIG. 2 is a side elevational view, partly in section, of an implantable T-shaped device including a porous titanium coating in accordance with the present invention, with intermediate polymeric vessel grafts.

As an alternative to polymeric collar member 29 device 10 may have a matte finish of titanium in the region of collar 29. Particularly advantageous is a coating 30 of porous titanium applied to the exterior subcutaneous surfaces of device 10 as shown in FIGS. 2 and 3. Coating 30 is limited to the subcutaneous portion of stem 11, as shown in FIGS. 2 and 3, for the same reason that collar 29 in FIG. 1 is so limited. A porous titanium coating may be applied by fusing titanium powder to the surfaces of the device. Pore size should be sufficient to permit tissue ingrowth but not so large that adhesion is lost.

The porous titanium coating 30 has the advantage that it facilitates tissue ingrowth and yet is it much less bulky than a polymeric collar member as shown in FIG. 1. Typically, a collar 29 of polyethylene-terephthalate will be approximately 0.1 inch thick, including adhesive layer, whereas an effective porous titanium coating 30 may be only 10–20% of that thickness. Furthermore, since the body of device 10 is also preferably titanium, there is a net reduction in foreign materials implanted under the skin. Both collar member 29 and the adhesive holding member 29 to device 10 are eliminated.

FIG. 2 shows a device coated with porous titanium for use with artificial polymeric vessel grafts 14. The coating layer does not extend to the ends of straight tube portion 12 under the grafts because the presence of a porous layer between the graft and body 10 would permit blood leakage and/or provide a site for blood clot formation. A smooth sealing surface under grafts 14 on the ends of straight tube portion 12 is, therefore, desirable.

Porous titanium coating 30 is most beneficial when device 10 is to be directly implanted into the circulatory system without use of artificial vessel grafts 14. The reduced bulk and lack of an exposed adhesive layer allow the porous coating to be extended to the ends of the portion 12 under vessels 32, as shown in FIG. 3, where the coating comes in contact with blood flowing through device 10. With porous titanium layer between natural vessels 32 and device 10 initial blood seepage and clotting within the porous layer will gradually be replaced by ingrowth of the vessel wall tissue so that the implant is securely anchored and there is a reduced likelihood of leakage or rupture at the vessel/implant interface.

Direct implantation of body 10 also provides the advantage that implantation is less traumatic and that elimination of vessel grafts 14 further reduces foreign material implanted below the skin. For example, trauma may be reduced by direct implantation because one way implantation can be accomplished is to provide an appropriately located incision, connect body 10 to suitable vessels, insert the body into the incision and close the incision around the body exterior portion of stem 11. By contrast, implantation of the device with polymeric grafts 14 typically involves providing a first incision through the skin into the body, connecting grafts 14 to the circulatory system, tunneling under the skin to a second incision and pulling the device by means of suture material wrapped around body 10 through the tunnel until stem 11 is pulled up through the second incision.

Although a porous titanium coating is the preferred embodiment of the present invention, other titanium matte finishes, such as an abraded surface or a titanium mesh coating, may also be used to facilitate tissue ingrowth and are considered to be within the scope of the present invention.

Blood access devices having the titanium matte finishes of the present invention may also advantageously be provided with a thin surface coating of vapor deposited carbon to further enhance biocompatibility. A several angstrom coating of vapor deposited carbon over the preferred porous titanium coating may be applied so that the carbon permeates the coating structure thereby retaining the desired porous surface structure as shown in FIGS. 2 and 3.

I claim:

1. An implantable blood access device for providing access to the circulatory system comprising a rigid body of biologically compatible material, said body having a generally T-shaped tubular configuration with the stem of the T joined to and in fluid communication with the arms of the T, said stem having a substantially constant outer diameter from the junction of the stem and the arms of the T to at least the excutaneous portion of the stem, an elastomeric septum member supported within the cavity of the stem, and removable retaining means for holding the septum with the stem in sealed relationship therewith, wherein said rigid body has a matte titanium finish on at least a portion of the subcutaneous exterior surfaces of the device and wherein said matte finish is limited to said subcutaneous surfaces.

2. A device as in claim 1 wherein said rigid body is made of titanium.

3. A device as in claim 1 or in claim 2 wherein said matte titanium finish comprises a coating of porous titanium.

4. A device as in claim 3 wherein the porous titanium coating is made of fused titanium powder.

5. A device as in claim 3 wherein the porous titanium coating extends along the outer tube surfaces of the arms of the T to the remote ends thereof.

6. A device as in claim 1 or claim 2 wherein the matte titanium finish is a layer of titanium mesh.

7. A device as in claim 2 wherein the matte titanium finish is an abraded surface on said rigid body.

8. A device as in claim 1 or claim 2 wherein said rigid body includes a coating of vapor deposited carbon on the surfaces thereof over said matte finish.

* * * * *